US00PP17402P2

(12) United States Plant Patent
Kordes

(10) Patent No.: US PP17,402 P2
(45) Date of Patent: Feb. 6, 2007

(54) MINIATURE ROSE PLANT NAMED 'KORSPUNTY'

(50) Latin Name: *Rosa hybrida*
Varietal Denomination: KORspunty

(75) Inventor: Tim-Hermann Kordes, Offenseth-Sparrieshoop (DE)

(73) Assignee: W. Kordes'Sõhne Rosenschulen GmbH & Co KG, Offenseth-Sparrieshoop (DE)

( * ) Notice: Subject to any disclaimer, the term of this patent is extended or adjusted under 35 U.S.C. 154(b) by 35 days.

(21) Appl. No.: 11/155,408

(22) Filed: Jun. 17, 2005

(51) Int. Cl.
*A01H 5/00* (2006.01)

(52) U.S. Cl. ..... Plt./118
(58) Field of Classification Search ..... Plt./118, Plt./104
See application file for complete search history.

*Primary Examiner*—Howard J. Locker

(57) ABSTRACT

A new and distinct variety of miniature rose with long lasting, novel yellow flowers, and dark green and attractive foliage. It exhibits compact, uniform growth and flowering under greenhouse conditions when grown as a potted floral plant. The new variety propagates well from cuttings and by grafting. This new and distinct variety has shown to be uniform and stable in the resulting generations from asexual propagation.

1 Drawing Sheet

Genus, species and variety denomination: The botanical classification of the new rose plant is *Rosa hybrida,* var. 'KORspunty'.

BACKGROUND OF THE INVENTION

The new variety of miniature rose plant of the present invention originated from a controlled crossing in a breeding program between 'KORengir' and an un-named seedling.

The two parents were crossed and the resulting seeds were planted in a controlled greenhouse environment. The resulting seedlings exhibited distinctive physical and biological characteristics. The new rose plant was selected in as a single plant from the seedling beds due to its superior characteristics and asexually propagated for further evaluation. This new and distinctive miniature rose variety is named 'KORspunty'.

SUMMARY OF THE INVENTION

The new rose plant may be distinguished from its seed parent, KORengir, by the following combination of characteristics:

1. The applicant variety has yellow flowers and the seed parent variety has orange flowers, and
2. The shape of the open flowers of the applicant variety is high-centered while the shape of the open flower of the seed parent variety is flat.

The new rose plant may be distinguished from its pollen parent, an un-named seedling by the following combination of characteristics:

1. The applicant variety typically exhibits one flower per flowering shoot while the pollen parent exhibits multiple flowers per flowering shoot,
2. The growth habit of the applicant variety is compact while the growth habit of the pollen parent variety is vigorous.

The objective of the hybridization was to create a new and distinct rose plant with unique qualities, such as:

1. Compact and uniform growth and flowering under greenhouse conditions when grown as a potted floral plant;
2. Abundant, long lasting, and attractive yellow flowers on upright stems;
3. Resistance to diseases encountered in greenhouse and nursery culture; and
4. Suitability for production from softwood cuttings in floral and nursery containers;

This combination of qualities is not present in prior rose cultivars. These objectives have been substantially achieved and in that distinguish 'KORspunty' from all other varieties of which we are aware.

As part of the rose development program, Tim-Hermann Kordes germinated the seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORspunty' was selected in May, 2001 from the seedling beds to be asexually propagated for further evaluation. The first asexual reproduction of 'KORspunty' was done by rooting softwood cuttings in July, 2001 at the Rosa-Danica Nursery in Odense, Denmark.

This initial and other subsequent propagations conducted in controlled environments show that the foregoing and all other characteristics of 'KORspunty' come true to form and are transmitted through succeeding generations.

BRIEF DESCRIPTION OF THE DRAWING

The accompanying color illustration shows as true as is reasonably possible to obtain in color photographs of this type, the typical characteristics of the buds, flowers, leaves, and stems of 'KORspunty'. Specifically illustrated in Sheet One:

FIG. 1. Stem with leaves and bud;

FIG. 2. Bud and partially opened flower bloom;

FIG. 3. Flower petals, detached;

FIG. 4. Dissected receptacle and detached sepals;

FIG. 5. Two sections of stem; and

FIG. 6. Two leaves.

DETAILED BOTANICAL DESCRIPTION

The following is a description of 'KORspunty', as observed in its growth in May, 2005 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORbritta', a rose variety from the same inventor described and illustrated in U.S. Plant Pat. No. 11,146 and issued on Dec. 7, 1999 are compared to 'KORspunty' in Chart 1.

CHART 1

| | 'KOR'spunty' | 'KORbritta' |
|---|---|---|
| Bud color | Yellow Group 9A. | Yellow Orange Group 21A. |
| Partially open flower | Yellow Group 9A. | Yellow Orange Group 21A. |
| General tonality. | Yellow Group 9B. | Yeflow Orange Group 21B. |

Parents:

*Seed parent.*—'KORengir'.

*Pollen parent.*—'An un-named seedling'.

Classification:

*Botanical classification.*—*Rosa hybrida,* var. 'KORspunty'.

*Commercial classification.*—Miniature rose.

FLOWER AND FLOWER BUD

Blooming habit: Recurrent.

Flower bud:

*Size.*—Upon opening, 30 mm in length from base of receptacle to end of bud.

*Bud form.*—Short to long pointed ovoid.

*Bud color.*—As sepals first unfold, bud color is Yellow Group 9A. When ¼ open, the color is Yellow Group 9A.

*Sepals.*—Size: Average 30–35 mm long×8–10 mm wide. Shape: Strong foliaceous appendages on three of the five sepals. Sepal apex comes to a long narrow point. Base is flat at union with receptacle. Quantity: Five. Surface texture: The surfaces of the sepals are moderately to slightly pubescent. Stipitate glands are present on margins of those sepals with appendages. Color: Upper surface Green Group 138A. Lower surface Green Group 138B.

*Receptacle.*—Surface: Smooth. Color: Green Group 138A. Shape: Pear. Size: 6–8 mm (h)×9–11 mm (w).

*Peduncle.*—Surface: Smooth with a limited number of fine white hairs. Length: 20–30 mm average length. Diameter: 2.0–2.5 mm average diameter. Color: Yellow-Green Group 146B. Strength: Strong. Borne: Multiple flower buds per stem, generally 5 to 9. Anthocyanin is present. Greyed-Red Group 181B.

Flower bloom:

*Fragrance.*—None to light.

*Duration.*—Long lasting. A blooming plant with flowers has a commercial shelf life of 6 to 12 days. The blooms have duration on the plant of approximately 10 to 14 days. As a cut flower, 4 to 8 days.

*Size.*—Medium. Average flower diameter is 35 mm when open.

*Form.*—Shape of flower when viewed from the side: Upon opening, upper part: Convex. Upon opening, lower part: Flattened convex. Open flower, upper part: Flattened convex. Open flower, lower part: Flat.

Color:

*Upon opening, petals.*—Outermost petals: Outer Side: Yellow Group 9A. Inner Side: Yellow Group 9A. Innermost petals: Outer Side: Yellow Group 9A. Inner Side: Yellow Group 9A.

*Upon opening, basal petal spots.*—Basal petal spot, outermost petals: Outer Side: Yellow Group 9A. Inner Side: Yellow Group 9A. Basal petal spot, innermost petals: Outer Side: Yellow Group 9A. Inner Side: Yellow Group 9A.

*After opening, petals.*—Outermost petals: Outer Side: Yellow Group 9B. Inner Side: Yellow Group 9B. Innermost petals: Outer Side: Yellow Group 9B. Inner Side: Yellow Group 9B.

*After opening, basal petal spots.*—Basal petal spot, outermost petals: Outer Side: Yellow Group 9B. Inner Side: Yellow Group 9B. Basal petal spot, innermost petals: Outer Side: Yellow Group 9B. Inner Side: Yellow Group 9B. Variegations: None.

General tonality: On an open flower Yellow Group 9B. No change in the general tonality at the end of the 4th day. Afterwards, general tonality is Yellow Group 9C.

Petals:

*Petal count.*—Very double. Approximately 50–60 petals under normal conditions with 10 petaloids.

*Petal reflex.*—Petals reflex slightly.

*Petal edge.*—Entire.

*Petal shape.*—Apex shape is round. Shape of base is deltoid with point of attachment.

*Petal size.*—20–25 mm long; 20–25 mm wide.

*Thickness.*—Average.

*Petal arrangement.*—Generally in a regular pattern with overlapping edges.

*Petaloids.*—Present. Average of 10 per flower. Petaloids are 10–15 mm long and 4–5 mm wide. Color of inner side is Yellow Group 9A. Color of outer side is Yellow Group 9A. Surface texture is smooth. Shape is linear.

Reproductive organs:

*Pistils.*—Average. Approximately 35–45 present. Length 10–15 mm. Stigmas: Location: Inferior in location to anthers. Color: Yellow-Green Group 150D. Styles: Color: Yellow-Green Group 150D.

*Stamens.*—Approximately 35–45 on average and regularly arranged around the styles. Anthers: Size: 3 mm long. Color: Yellow Group 1A. Quantity: Approximately 35–45. Pollen: Generally present. Color: Yellow Group 1A. Filaments: Color: Yellow Group 12A. Length: 5–6 mm. Quantity: Approximately 35–45.

THE PLANT

Plant growth: Moderate vigor. Compact. When grown as a 10 cm pot plant, the average height of the plant itself is 16–18 cm and the average width is 14–16 cm. When grown as a budded field plant on multiflora understock the average plant height is 35–45 cm and the average plant width is 30–40 cm.

Stems:

*Stem color.*—Young wood: Green Group 143C. Older wood: Green Group 137C.

*Stem surface.*—Young wood: Smooth. Older wood: Smooth. Anthocyanin is present. Color: Greyed-Red Group 179B.

Prickles: Present.

*Incidence.*—Variety has limited numbers of thorns on the upper half of the plant.

*Size.*—Average length: 3 mm.

*Color.*—Greyed-Orange Group 166B.

*Shape.*—Linear to downward hooked.

Leaves and leaflets: Normally 5 leaflets on normal leaves in the middle of the stem.

*Leaf size.*—110 mm (l)×85 mm (w).

*Quantity.*—Average.

*Texture.*—Matte finish. Smooth.

*Color, mature foliage.*—Upper Leaf Surface: Green Group 137A. Lower Leaf Surface: Green Group 138A.

*Color, juvenile foliage.*—Upper Leaf Surface: Green Group 137A. Lower Leaf Surface: Green Group 138A.

*Anthocyanin intonation.*—Present, but limited in expression. Location: On juvenile foliage and stems. Color Greyed-Red Group 179B.

Stipules:

*Size.*—20–22 mm (l) — 8–12 mm (w).

*Stipule color.*—Green Group 139A. Some intonations of Greyed-Red Group 179B.

*Presence of stipitate glands.*—Present on margins.

Petiole:

*Length.*—25 mm–30 mm.

*Diameter.*—1.5 mm average diameter.

*Petiole color.*—Green Group 139A. Underneath: smooth with a few white hairs. Anthocyanin: Present. Color Greyed-Red Group 179B.

*Prickles.*—Generally absent.

*Stipitate glands.*—Present on margins.

Petiole rachis:

*Color.*—Green Group 139A. Underneath: smooth with very few white hairs. Margins: with stipulate glands. Anthocyanin: Present. Color Greyed-Red Group 179B.

*Prickles.*—Generally absent.

*Stipitate glands.*—Present on margins.

Leaflets:

*Size.*—Average size of the terminal leaflet is 40 mm (l)×30 mm (w).

*Shape.*—Ovate.

*Margins.*—Finely serrated.

*Texture.*—Thick.

*Arrangement.*—Odd pinnate.

Hips/seed formation: None observed.

Winter hardiness: Due to the variety's principal use in greenhouses, winter hardiness has not been evaluated.

Disease resistance: Above average resistance to mildew and Botrytis under normal growing conditions.

I claim:

1. A new and distinct variety of miniature rose plant characterized by the following combination of characteristics:

(a) forms abundant, attractive long lasting yellow flowers;

(b) exhibits a compact and bushy growth habit;

(c) is suited for growing in greenhouse in pots from softwood cuttings, and;

(d) exhibits durable flowers and foliage suitable for distribution in the floral industry;

substantially as herein illustrated and described.

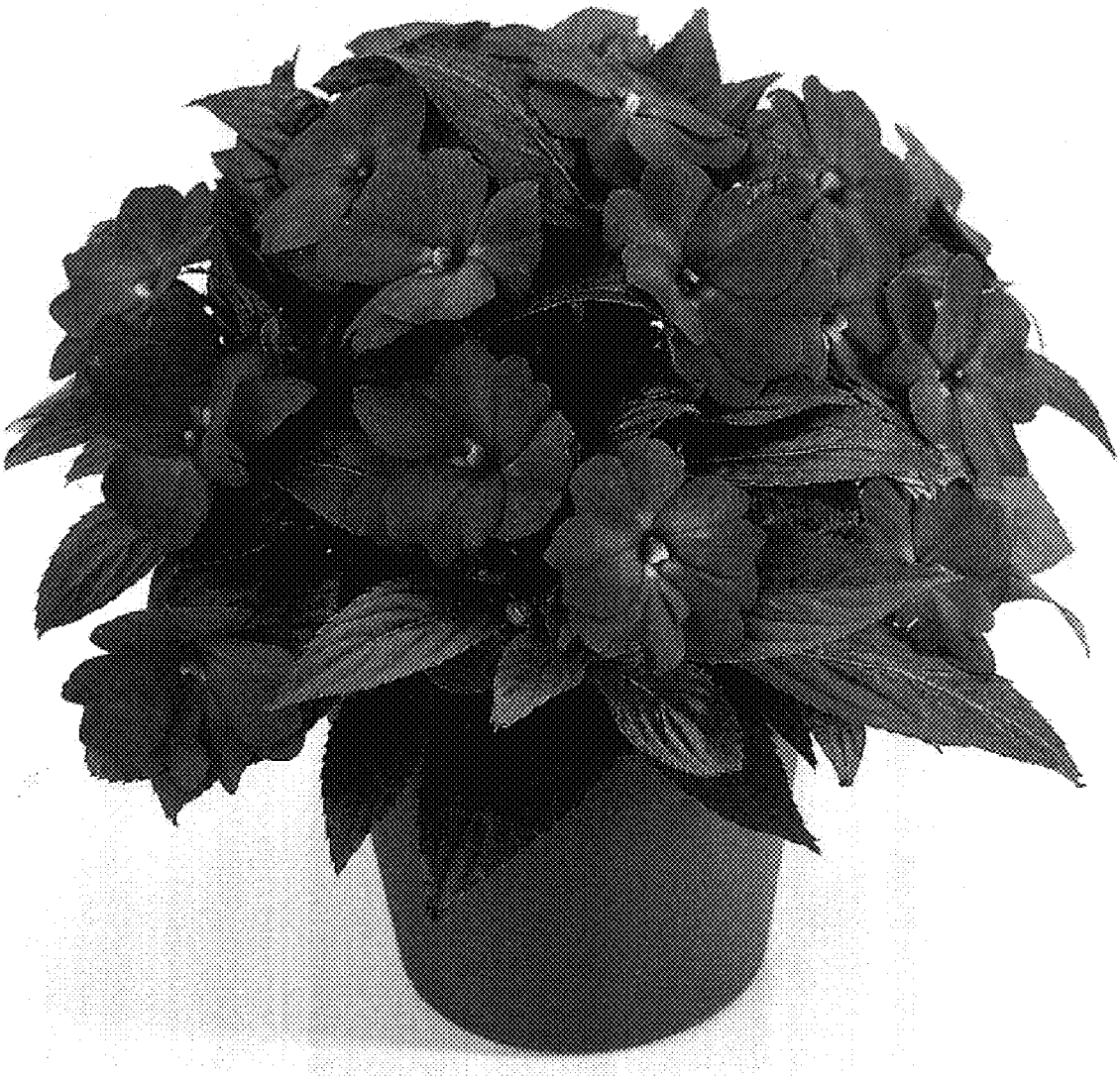

* * * * *